(12) United States Patent
Joffe

(10) Patent No.: US 6,431,010 B1
(45) Date of Patent: Aug. 13, 2002

(54) OPTICAL FIBER-BASED FLUID FLOW ANEMOMETER

(76) Inventor: Michael A. Joffe, 25 Alderbrook Ct., Wrentham, MA (US) 02093

( * ) Notice: Subject to any disclaimer, the term of this patent is extended or adjusted under 35 U.S.C. 154(b) by 0 days.

(21) Appl. No.: 09/036,975

(22) Filed: Mar. 9, 1998

(51) Int. Cl.$^7$ .................................................. G01F 1/00
(52) U.S. Cl. ....................................................... 73/861
(58) Field of Search .............................. 73/204.11, 355, 73/349, 362, 861; 356/28, 28.5; 250/356.1

(56) References Cited

U.S. PATENT DOCUMENTS

| | | | |
|---|---|---|---|
| 3,620,207 A | | 11/1971 | Sinclair |
| 3,789,831 A | | 2/1974 | Kopaniky |
| 3,960,017 A | * | 6/1976 | Romanowski ................ 73/349 |
| 4,016,761 A | * | 4/1977 | Rozzell et al. ................. 73/356 |
| 4,111,050 A | * | 9/1978 | Waddoups .................... 73/362 |
| 4,354,504 A | | 10/1982 | Bro |
| 4,677,985 A | | 7/1987 | Bro |
| 5,174,299 A | | 12/1992 | Nelson |
| 5,207,227 A | | 5/1993 | Powers |
| 5,373,850 A | | 12/1994 | Kohno |
| 5,509,424 A | | 4/1996 | Al-Ali |
| 5,582,628 A | | 12/1996 | Wood |
| 5,617,870 A | | 4/1997 | Hastings |
| 5,865,871 A | * | 2/1999 | Simundich ................... 73/861 |

OTHER PUBLICATIONS

Regional Cortical Blood Flow at Craniotomy Carter et al, May Jun. 1978 Neurosurgen vol. 2 No. 3.
Blood Flow Measurements: Future Applications & Prospects, Rushmer Med Inst, vol. 11, No. 3 May Jun. 1977.
A Thermoelectric Blood Flow Recorder in the Form of a Needle, Subbs.
Measurement of the Velocity of Blood Flow (in vivo) Using a Fibre Catheter & Optical Mixing Spectroscopy, Tanaka & Benedek app op vol. 14, No. 1, Jan. '75.
Thermal Method for Continuous Blood Velocity Measurements in Large Blood Vessels and Cardiac Output determination, Med & Bio Engr, Mar. '73.
Measurement of Cardiac Output Using Near–Infared healing of Blood Curley et al, SPIE vol. 2970 •2799–786X/97.

* cited by examiner

*Primary Examiner*—Benjamin R. Fuller
*Assistant Examiner*—Jewel V. Thompson
(74) *Attorney, Agent, or Firm*—John R. Ross; John R. Ross, III

(57) ABSTRACT

A fluid flow monitoring device. A laser source produces a laser beam having a beam frequency that is transmitted through an optical fiber and absorbed in a small quantity of thermally conductive material having high optical absorption at the beam frequency. A temperature sensor is embedded in the light absorbing material. The light absorbing material is placed in a fluid flow and the light absorbing material is heated with energy in the laser beam. Voltage produced by the temperature sensor is monitored as an indication of the fluid flow. The flow-measuring device can be made extremely unintrusive using very thin temperature sensor wire and very thin optical fiber, both of which are contained within a very thin probe. The device is calibrated under known flow conditions. The flowing fluid cools the material. Using the calibration information, speed of the flowing fluid is determined by measuring the voltage produced by the temperature sensor.

17 Claims, 5 Drawing Sheets

OPTICAL FIBER-BASED FLUID FLOW ANEMOMETER

The present invention relates to flow meters and in particular to flow meters operating on heat transfer principles.

BACKGROUND OF THE INVENTION

There are many devices available for measuring fluid flow. It has been well known for centuries that increased fluid flow increases the rate of cooling of a hot object disposed in a flow stream. Several devices have been proposed for measuring flow, which make use of this principle, known as anemometry. The following U.S. patents disclose such devices:

U.S. Pat. No. 5,617,870, issued to Hastings and Feld
U.S. Pat. No. 5,582,628, issued to Wood X
U.S. Pat. No. 5,508,424, issued to Al-Ali
U.S. Pat. No. 5,373,850, issued to Kohno
U.S. Pat. No. 5,207,227, issued to Powers
U.S. Pat. No. 5,174,299, issued to Nelson
U.S. Pat. No. 4,677,985, issued to Bro and Carter
U.S. Pat. No. 4,354,504, issued to Bro
U.S. Pat. No. 3,789,831, issued to Kopaniky and Gann
U.S. Pat. No. 3,620,207, issued to Sinclair In these devices, heat is typically provided with a resistance element. Some of these devices are proported to be minimally intrusive and are proposed for use in measuring blood flow in large veins and arteries. It is known that optical fibers with very small diameters are available and it is also known that thermocouple wire can be made of very small diameter material.

Resistive heaters used in prior art anemometers are larger than about 1 mm. Because of their size, the prior art flow probes cannot be used in small fluid pipes, such as small blood vessels. The relatively large size of the prior art probes does not allow enclosing those into a needle for measuring blood flow through capillary tissue or through porous media. Furthermore, for measuring flow of combustible or explosive fluids, such as underground oil or gas, it is highly undesirable to use electric heating for safety reasons.

What is needed is a less intrusive and safer than prior art flow measuring device.

SUMMARY OF THE INVENTION

The present invention provides a fluid flow monitoring device. A laser source produces a laser beam having a beam frequency that is transmitted through an optical fiber and absorbed in a small quantity of thermally conductive material having high optical absorption at the beam frequency. A temperature sensor is embedded in the light absorbing material. The light absorbing material is placed in a fluid flow and the light absorbing material is heated with energy in the laser beam. Voltage produced by the temperature sensor is monitored as an indication of the fluid flow. The flow-measuring device can be made extremely unintrusive using very thin temperature sensor wire and very thin optical fiber, both of which are contained within a very thin probe. The device is calibrated under known flow conditions. The flowing fluid cools the material. Using the calibration information, speed of the flowing fluid is determined by measuring the voltage produced by the temperature sensor.

DETAILED DESCRIPTION OF PREFERRED EMBODIMENTS

Preferred embodiments of the present invention may be described by reference to the drawings.

Prototype System

Figure 1:
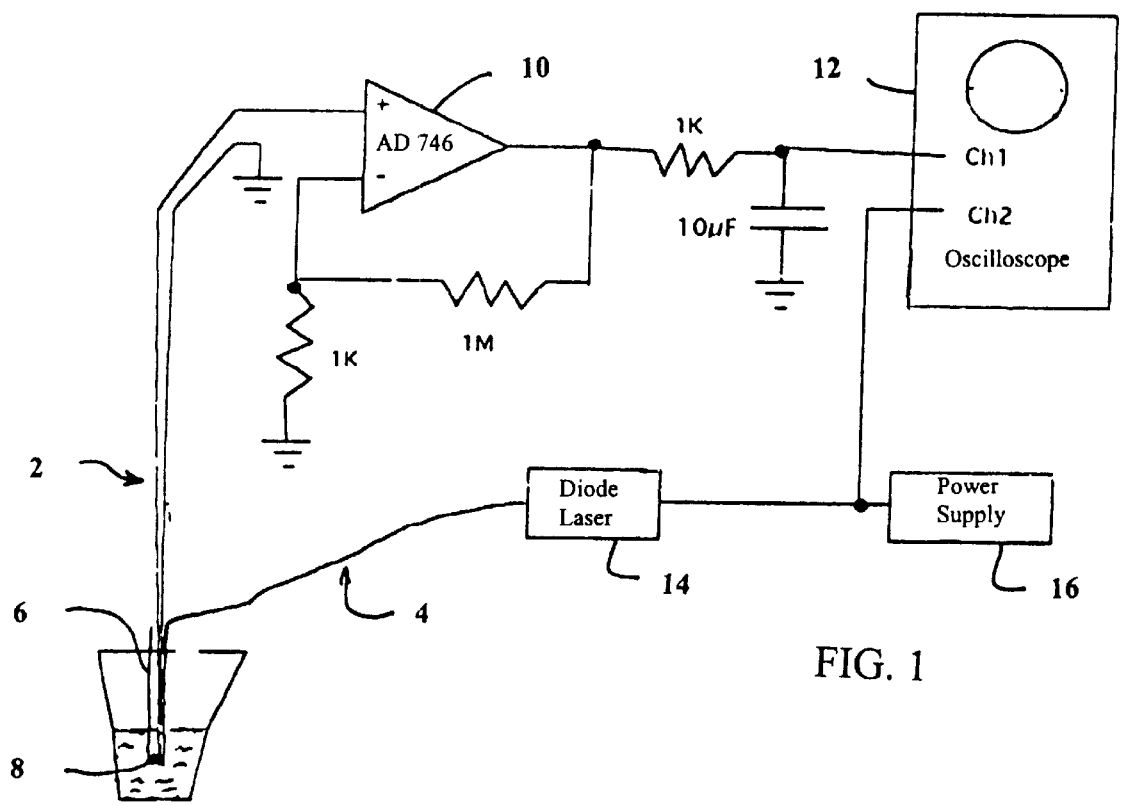
FIG. 1 is a drawing of a preferred embodiment of the present invention.

A first preferred embodiment of the present invention is a prototype system built by Applicant to prove the feasibility of the present invention. The system is shown in FIG. 1. A thin thermocouple element with lead wires 2 (Model 5TC-TT-K-36-36, available from Omega Engineering with offices in Stamford, Conn.) and optical fiber 4 (Model FG-200-LCR, available from 3M Specialty Optical Fibers with offices in West Haven, Conn.) are inserted into a 20 gauge Teflon tube (0.9 mm I.D.) 6. The heat sensitive end of thermocouple 2 and the distal end of optical fiber 4 are positioned in close proximity to each other near the tip of Teflon tube 6. A 1-mm long section at the tip of tube 6 of tube 6 is filled with about 0.5 microliter of black, optically opaque, thermally conductive epoxy 8 (Model H62, available from Epoxy Technology, Inc. with offices in Billerica, Mass.). The tips of both the thermocouple 2 and the optical fiber 4 are imbedded in the epoxy.

Figure 2:
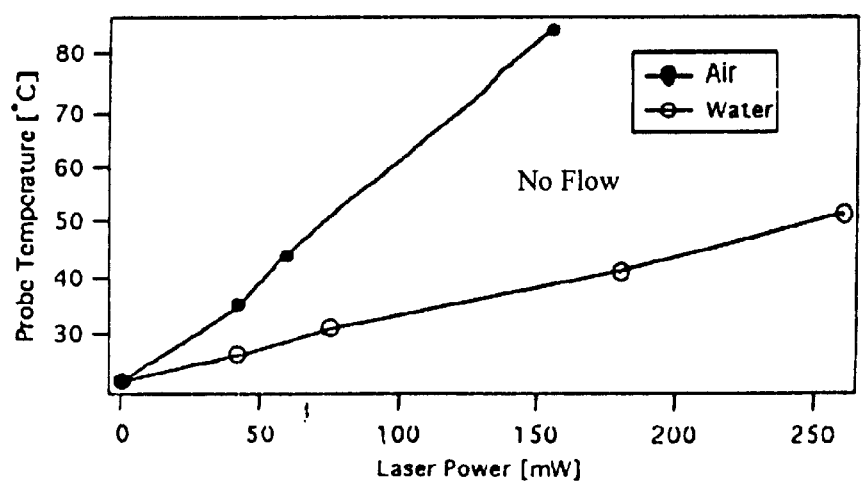
FIG. 2 is a graph showing probe temperature as a function of laser power for a preferred embodiment of the present invention.

The output voltage of thermocouple is amplified by an AD746 operational amplifier 10 configured to provide a gain of about 1000 and the output of the amplifier is filtered and displayed on oscilloscope 12. A diode laser 14, which in this embodiment is a Model 2320 from SDL, Inc. with offices in San Jose, Calif., provides a laser beam of about 250 mW to optical fiber 4, substantially all of which is absorbed initially in epoxy 8 which heats the tip of tube 6 to a temperature of interest. Laser 12 is driven by regulated power supply 16 (which is a Model 3610A power supply available from Hewlett-Packard with offices in Palo Alto, Calif.). Adjusting the output of power supply 16 controls the output power of laser 14. FIG. 2 is a graph showing steady state temperature of the probe tip as a function of laser power with the tip immersed in still water and with the tip immersed in still air.

Figure 3:
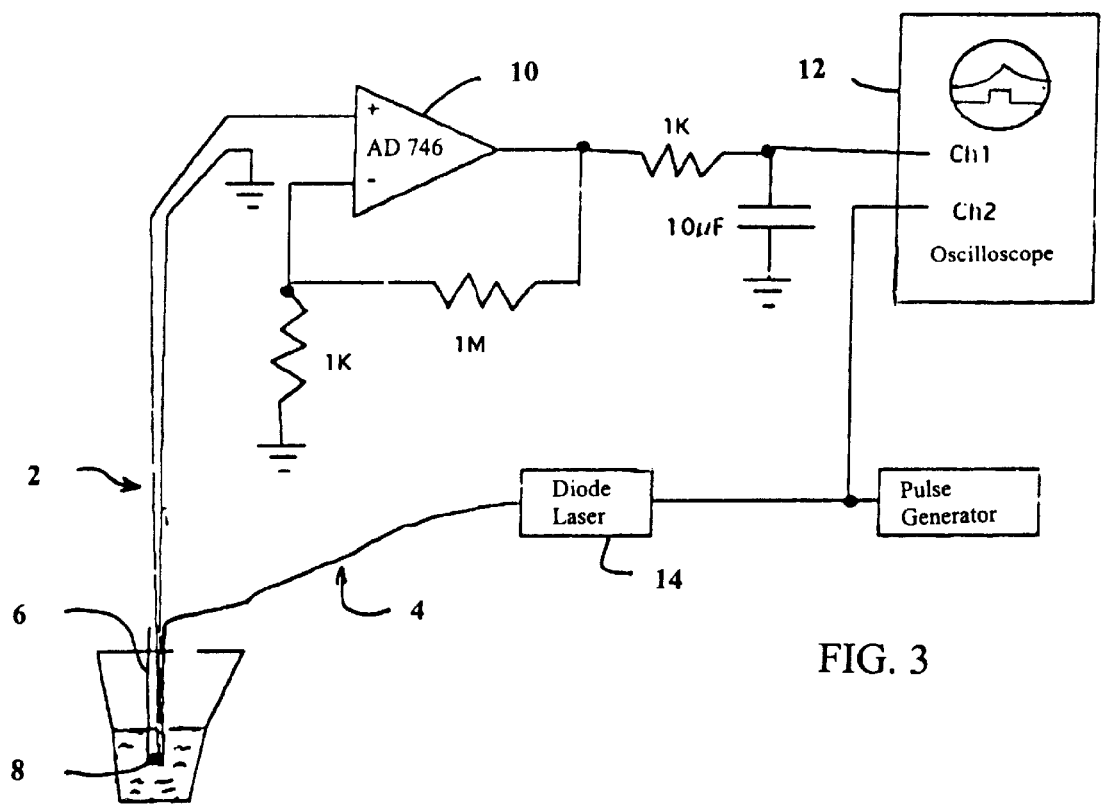
FIG. 3 is a second preferred embodiment of the present invention.
Figure 4:
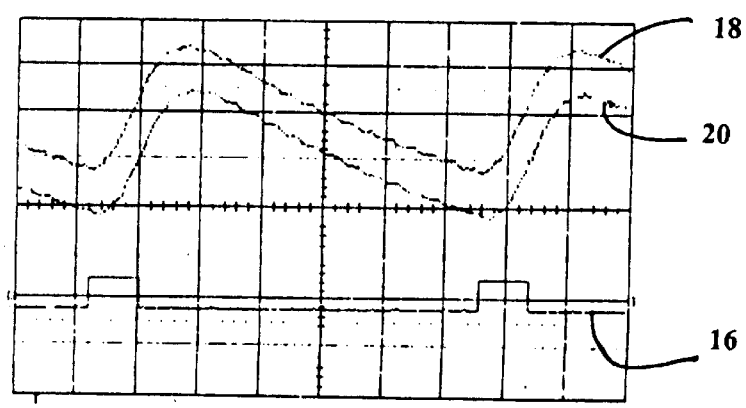
FIG. 4 is a graph of experimental data with a preferred embodiment operation in a pulse mode.

FIG. 3 is a graph showing thermocouple output with the laser operated in a pulsed mode with 50 ms; 10 mJ pulses with the probe tip in water. Plot 16 is the 50 ms pulse, plot 18 is the thermocouple output at 0 flow and plot 20 is the thermocouple output at 10 cm/s flow. From these plots it is clear that flow can be determined based on the peak temperature following a pulse. The estimated accuracy of this prototype device is about 0.5 cm/s. Flow could also be calculated based on the shape of the thermocouple output signal trace following a pulse. For example, the time required for the resulting temperature to decrease by 50 percent would be a good measure of the fluid flow.

Blood Flow

Figure 5:
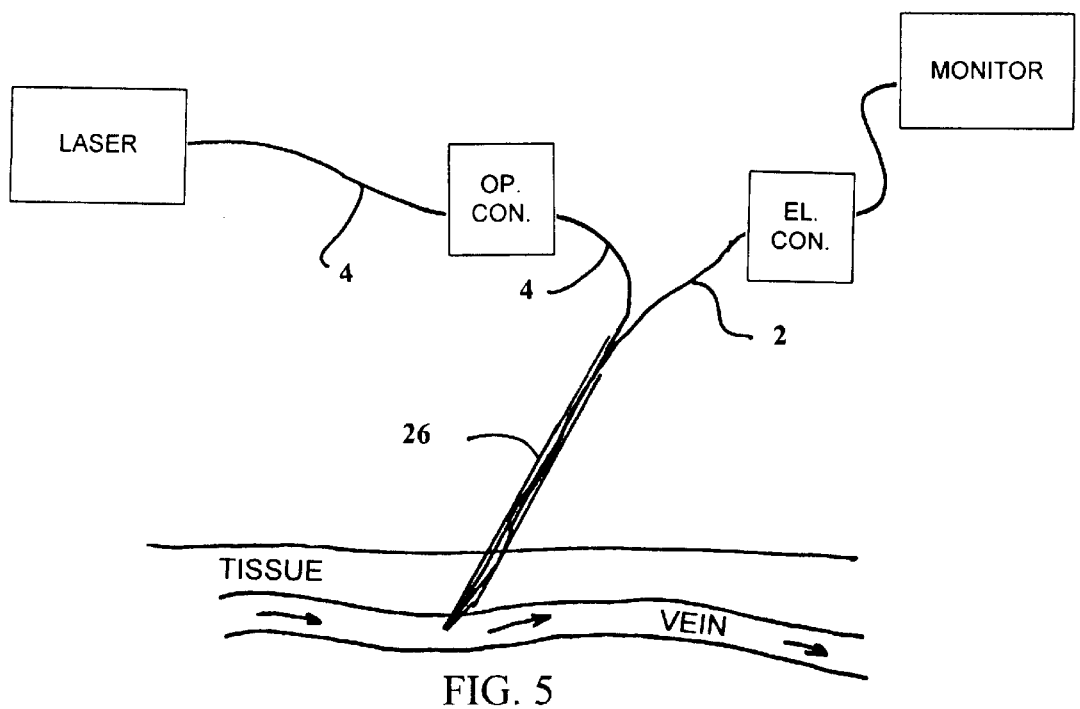
FIG. 5 is a drawing showing a blood speed-measuring device.

FIG. 5 shows a preferred embodiment for measuring blood flow. In this embodiment the thermocouple and optical fiber are inserted in a hypodermic needle 26 and extended to the tip of the needle and the hot junction of the thermocouple and the tip of the optical fiber are encased in the thermally conductive compound 8 as shown in FIG. 5. Thermocouple wires with diameters of less than 25 microns are available and optical fibers with diameters of less than 50 microns are available. Therefore, these elements can be combined to form a probe having thickness dimensions approximately the size of three human hairs. (A typical human hair has a diameter of about 50 microns.) It should be noted that it is also possible to deliver the probe via a catheter.

Feedback Loop

Figure 6:
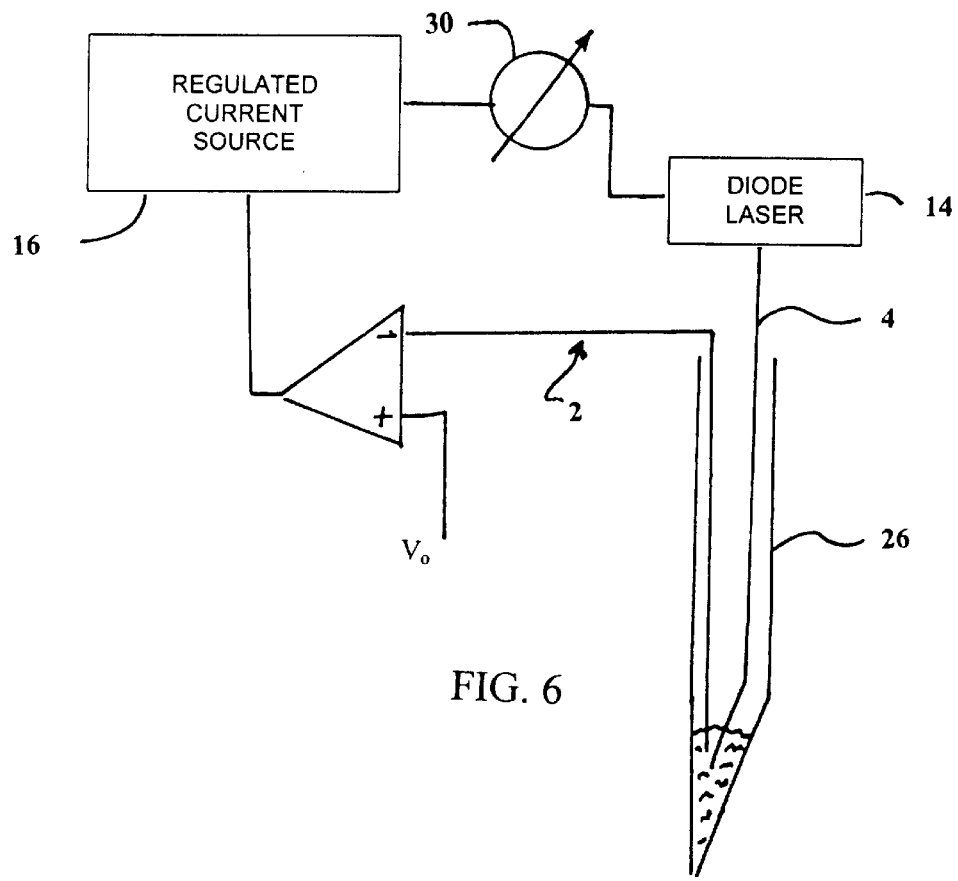
FIG. 6 is a drawing showing some of the elements of a preferred embodiment.

An embodiment of the present invention useful for measuring blood flow is shown in FIG. 6. This embodiment contains a feedback loop programmed to keep the tip of needle 26 at a constant temperature determined by Vo while the tip is cooled by flowing blood.

The current powering laser 14 as indicated by ammeter 30 is a function of the blood speed. As above the unit must be calibrated under known flow conditions. This preferred flow monitor includes of a control box incorporating the laser source, control electronics, power modules, and devices for recording and displaying data. The probe, disposable or reusable includes a thermocouple and an optical fiber, which are outfitted with standard electrical and optical connectors. These connectors permit reliable connections and easy replacement.

Prototype Testing

Figure 7:
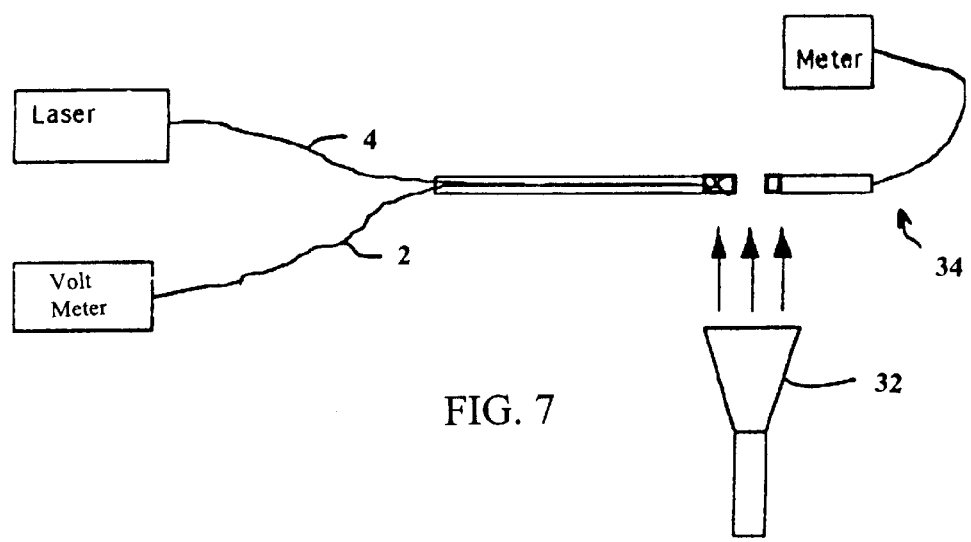
FIG. 7 shows a test-calibration setup.
Figure 8:
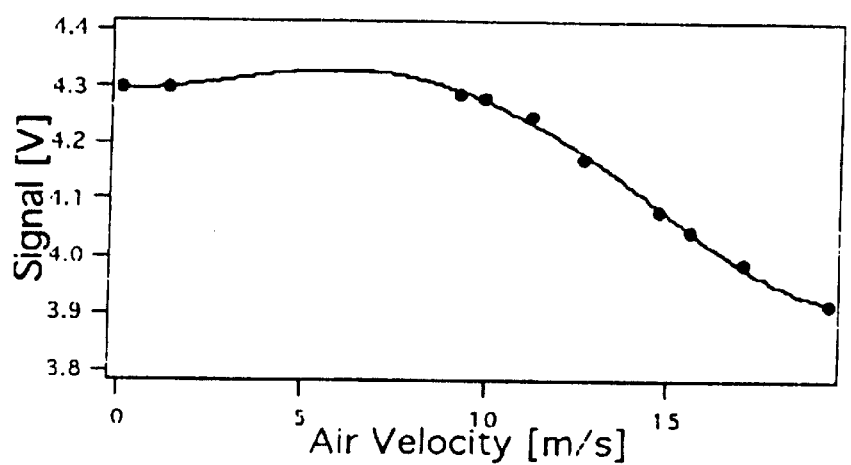
FIGS. 8 and 9 show graphs of test data.

A prototype test setup is described in FIG. 7. This setup includes a compressed air nozzle 32. A standard pressure regulator not shown provides compressed air flow. A prior art airflow probe 34 (TSI Inc, Model 8330-M) is placed adjacent to the probe of the present invention, which is the same probe described with reference to FIG. 1. Test results are shown in FIG. 8.

Figure 9:
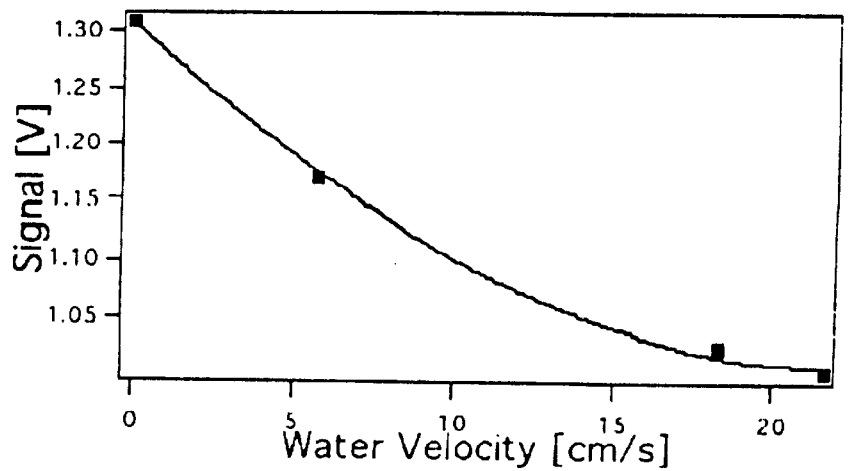

The same probe was tested as a liquid flow meter. The probe was placed inside a ⅜-inch tube and water was flowed through the ⅜-inch tube and the water is collected to determine the flow rate for calibrating the probe. The probe was heated with 200 mW of laser power. The results are shown in FIG. 9.

Figure 10:
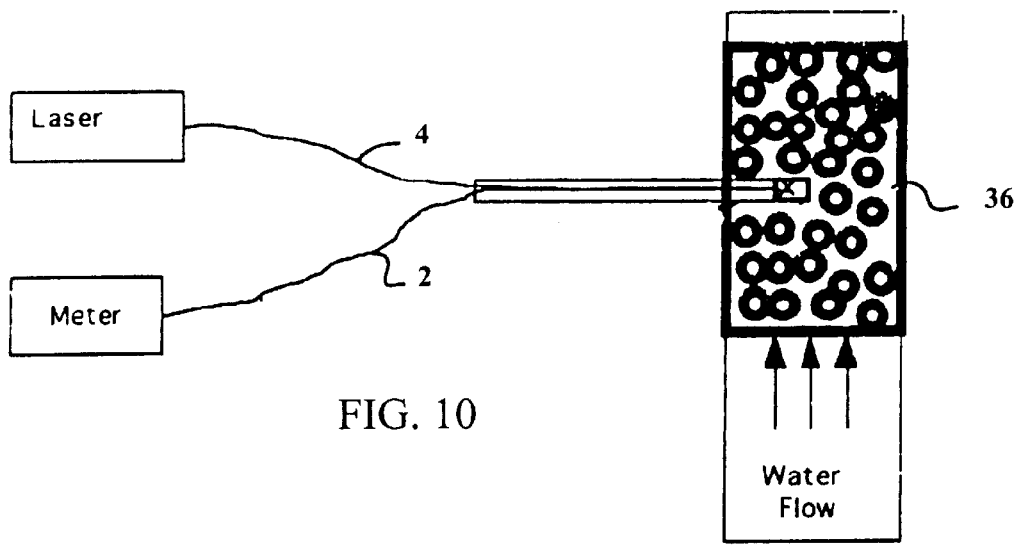
FIG. 10 shows a setup for testing a preferred embodiment for measuring underground flow.
Figure 11:
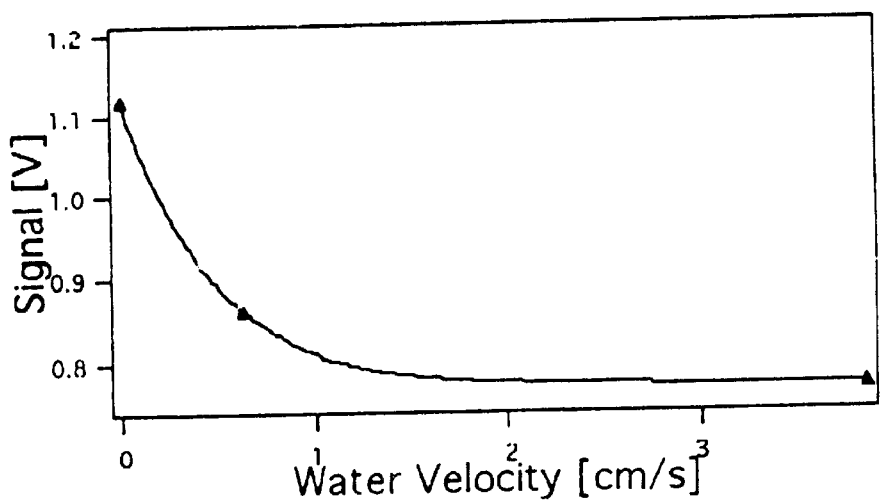
FIG. 11 is a graph of data from the FIG. 10 setup.

A potential use of the present invention is to measure underground fluid flow such as water or oil. The test setup is shown in FIG. 10. The probe is placed in a soil sample 36 through which water is flowed. The results are shown in FIG. 11.

The foregoing description of the present invention has been presented for the purpose of illustration and is not intended to limit the invention to the precise form disclosed. It is understood that many modifications and changes may be effected by those skilled in the art. For example, any temperature sensor can be used in the optical-fiber probe. Examples of temperature sensors include, but are not limited to, thermocouples, thermistors, RTDs, integrated circuit (IC) temperature sensors. A wide range of thermocouples, thermistors, and RTDs is commercially available, among others, from Omega Engineering with offices in Stamford, Conn. An example of an IC temperature sensor is model AD590 available from Analog Devices with offices in Norwood, Mass.

Thermocouples are the smallest sensors and have advantage for fabrication of small-diameter probes for minimally invasive medical application. Because of their non-linear output, thermocouples require common but sophisticated electronic meter. Further, because thermocouples have two temperature sensitive junctions, they demand a temperature compensation provision for the second junction outside the probe. The provisions are commonly known and used in prior art.

IC temperature sensors have advantage of linear electric output and can be easily interfaced with control electronics. They are larger in size than thermocouples, typically 2–5 mm, but small enough to be easily incorporated in the optical-fiber-based flow probe. Both thermocouples and IC sensors do not require external electric power for operation that makes them attractive for intrinsically safe applications, such as combustible fluid flow measurement.

Thermistors and RTDs are inexpensive sensors and are widely used for fluid temperature measurements. Output signal processing devices for these sensors is very well developed and commonly used, which makes them attractive for incorporation into optical fiber based flow probes.

Therefore, the scope of the present invention shall be limited only by the appended claims and their legal equivalents.

I claim:

1. A fluid flow monitoring device comprising:
  A) a laser source for producing a laser beam defining a beam frequency,
  B) a quantity of light absorbing material having a high optical absorption at said frequency and configured for placement in said fluid flow,
  C) an optical fiber for transmitting said laser beam to said light absorbing material wherein said laser beam when absorbed in the material causes a temperature rise in the material,
  D) a temperature sensor, having a temperature sensor element located in or adjacent to said light absorbing material, for sensing temperature in said light absorbing material and producing a signal indicative of said temperature, and
  E) a detector for detecting signals from said sensor;
  wherein said light absorbing material, when inserted into said fluid flow and illuminated by said laser beam, absorbs energy from said laser beam and is thereby heated by said laser beam and cooled by said fluid flow, experiences temperature changes indicative of said fluid flow which changes are sensed by said temperature sensor producing signals which are detected by said detector to monitor said fluid flow.

2. A device as in claim 1 wherein said temperature sensor is a thermocouple defining a first junction and a second junction, said first junction being embedded in said small quantity of light absorbing material.

3. A device as in claim 1 and further comprising a thin tube containing said small quantity of light absorbing material and at least a portion of said temperature sensor and a portion of said optical fiber.

4. A device as in claim 1 wherein said laser source is a diode laser.

5. A device as in claim 1 and further comprising a voltmeter to measure voltage generated by said temperature sensor.

6. A device as in claim 1 and further comprising a feedback circuit comprising a regulated power supply to supply current to said laser.

7. A device as in claim 6 and further comprising an ammeter to measure electrical current in said feedback circuit.

8. A device as in claim 1 and further comprising a pulse generator to cause said laser to produce laser pulses.

9. A device as in claim 1 wherein said small quantity of light absorbing material black thermally conductive epoxy.

10. A device as in claim 8 and further comprising a processor to derive fluid speed from the shape of temperature pulses output by said temperature sensor.

11. A device as in claim 1 wherein said light absorbing material is configured for placement in a blood vessel.

12. A device as in claim 11 and further comprising a hypodermic needle for placing said light absorbing material is a blood vessel.

13. A process for monitoring fluid flow in a fluid flow stream comprising the steps of:

A) inserting a quantity of light absorbing material in said fluid flow stream,

B) heating said material with a laser beam from a laser source transmitted through an optical fiber, and C) monitoring, with a temperature sensor in communication with a detector configured to detect signals from said sensor, said fluid flow by detecting temperature changes in said material caused by heating produced by said laser beam and cooling produced by said fluid flow.

14. A process as in claim 13 wherein said temperature sensor is a thermocouple.

15. A process as in claim 14 wherein said detector is a voltmeter.

16. A process as in claim 13 wherein said fluid flow stream is a blood flow stream in a blood vessel.

17. A process as in claim 16 wherein a hypodermic needle is used to insert said material in a said blood vessel.

* * * * *